US005652225A

United States Patent [19]

Isner

[11] Patent Number: 5,652,225
[45] Date of Patent: Jul. 29, 1997

[54] METHODS AND PRODUCTS FOR NUCLEIC ACID DELIVERY

[75] Inventor: Jeffrey M. Isner, Weston, Mass.

[73] Assignee: St. Elizabeth's Medical Center of Boston, Inc., Boston, Mass.

[21] Appl. No.: 675,523

[22] Filed: Jul. 3, 1996

Related U.S. Application Data

[63] Continuation of Ser. No. 318,045, Oct. 4, 1994, abandoned.

[51] Int. Cl.$^6$ ............................................. A01N 47/40
[52] U.S. Cl. ............................... 514/44; 604/51; 604/52; 604/53; 536/23.5; 536/23.51; 435/320.1; 435/172.1; 435/172.3; 935/9; 935/22; 935/32; 935/33; 935/34; 935/52; 935/57; 424/93.2
[58] Field of Search ............................. 514/44; 604/51, 604/52, 53; 536/23.5, 23.51; 435/320.1, 172.1, 172.3, 235.1, 240.2; 935/9, 22, 32, 33, 34, 52, 57; 424/93.2

[56] References Cited

U.S. PATENT DOCUMENTS

| | | | |
|---|---|---|---|
| 5,091,205 | 2/1992 | Fan | 427/2.28 |
| 5,252,479 | 10/1993 | Srivastava | 435/235.1 |
| 5,304,121 | 4/1994 | Sahatjian | 604/53 |
| 5,328,470 | 7/1994 | Nabel et al. | 604/101 |

FOREIGN PATENT DOCUMENTS

| | | |
|---|---|---|
| WO93/00051 | 1/1993 | WIPO. |
| WO93/00052 | 1/1993 | WIPO. |

OTHER PUBLICATIONS

Fram, et al., Circulation: vol. 86, No. 4, Oct., 1992. Abstract:1515.
Tischer, et al., The Journal of Biological Chemistry; vol. 266, No. 18, Issue of 6/25, pp. 11947–11954, 1991.
Chapman, et al., Circulation Research: vol. 71, No. 1, Jul. 1992, pp. 27–33.
Gal, et al., Circulation: vol. 85, No. 2, Feb. 1992, pp. 756–768.
Nabel, et al., Nature, vol. 362, Apr. 29, 1993, pp. 844–846.
Nabel, et al., Science, Reprint Series Sep. 14, 1990, vol. 249, pp. 1285–1288.
Nabel, et al., Reprint Series Jun. 16, 1989, Science, vol. 244, pp. 1342–1344.
Takeshita, et al., J. Clin.Invest.; vol. 93, Feb. 1994, 662–670.
Riessen, et al., "Human Gene Therapy" 4:749–758 (1993); Published Dec. 1993.
Isner & Rosenfield; Circulation: vol. 88, No. 4, Part 1, Oct. 1993, pp. 1534–1557.
Flugelman, et al., Circulation: vol. 85, No. 3, Mar. 1992, pp. 1110–1117.
Takeshita et al., Circulation: vol. 88, No. 4, Part 2, Oct. 1993; Abstract #1985, p. I-370.
Reissen, et al., Press Release Jul. 14, 1993.
Riessen, et al., European Heart Journal 14:78 (1993), p. 78.
Reissen, et al., Abstract: JACC 21:74A, 1993, American College of Cardiology 42nd Annual Scientific Session; Mar.14–18, 1993.
Barr & Leiden; TCM 282; Revised Oct. 14, 1993, pp. 57–63.
Steg, et al., Circulation, vol. 90, No. 4, (1994), pp. 1648–1656.

Primary Examiner—Christopher S. F. Low
Attorney, Agent, or Firm—David G. Conlin; David S. Resnick; Dike, Bronstein, Roberts & Cushman, LLP

[57] ABSTRACT

The present invention provides a method for the delivery of a nucleic acid to an arterial cell comprising contacting the cell with a hydrophilic polymer incorporating the nucleic acid. The nucleic acid may be any nucleic acid, including antisense DNA or RNA. The nucleic acid may encode hormones, enzymes, receptors or drugs of interest. The nucleic acid is selected based upon the desired therapeutic outcome. For example, in the treatment of ischemic diseases, one would select a DNA encoding an angiogenic protein. The nucleic acid may be carried by a microdelivery vehicle such as cationic liposomes and adenoviral vectors. DNA encoding different proteins may be used separately or simultaneously.

6 Claims, 7 Drawing Sheets

human VEGF sequence

Ile Glu Tyr Ile Phe Lys Pro
ATC GAG TAC ATC TTC AAG CCA

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown     ( x i ) SEQUENCE DESCRIPTION: SEQ ID NO:1:

```
GAGGGCAGAA TCATCACGAA GT                                         22
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown     ( x i ) SEQUENCE DESCRIPTION: SEQ ID NO:2:

```
TCCTATGTGC TGGCCTTGGT GA                                         22
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown     ( x i ) SEQUENCE DESCRIPTION: SEQ ID NO:3:

```
AGCCCGTCAG TATCGGCGGA ATTC                                       24
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown     ( x i ) SEQUENCE DESCRIPTION: SEQ ID NO:4:

```
CAGCTCCTCG GTCACATCCA G                                          21
```

METHODS AND PRODUCTS FOR NUCLEIC ACID DELIVERY

This is a continuation of application Ser. No. 08/318,045 filed on Oct. 4, 1994 now abandoned.

FIELD OF THE INVENTION

The present invention relates to delivery of nucleic acid to arterial cells and compositions therefor.

BACKGROUND OF THE INVENTION

Work from several laboratories (Nabel, et al., Science, 249:1285–1288 (1990); Lim, et al., Circulation, 83:2007–2011 (1991); Flugelman, et al., Circulation, 85:1110–1117 (1992); Leclerc, et al., J. Clin. Invest., 90:936–944 (1992); Chapman, et al., Circ. Res., 71: 27–33 (1992); Riessen, et al., Hum. Gene Ther., 4: 749–758 (1993); and Takeshita, et al., J. Clin. Invest., 93:652–661 (1994), has demonstrated that recombinant marker genes could be transferred to the vasculature of live animals.

Gene delivery systems employed to date have been characterized by two principal components: a macrodelivery device designed to deliver the DNA/carrier mixture to the appropriate segment of the vessel, and microdelivery vehicles, such as liposomes, utilized to promote transmembrane entry of DNA into the cells of the arterial wall. Macrodelivery has typically been achieved using one of two catheters initially developed for local drug delivery: a double-balloon catheter, intended to localize a serum-free arterial segment into which the carrier/DNA mixture can be injected, or a porous-balloon catheter, designed to inject gene solutions into the arterial wall under pressure. Jorgensen et al., Lancet 1:1106–1108, (1989); Wolinsky, et al., J. Am. Coil. Cardiol., 15:475–485 (1990); March et al., Cardio Intervention, 2:11–26 (1992)); WO93/00051 and WO93/00052.

Double balloon catheters are catheters which have balloons which, when inflated within an artery, leave a space between the balloons. The prior efforts have involved infusing DNA-containing material between the balloons, allowing the DNA material to sit for a period of time to allow transfer to the cells, and then deflating the balloons, allowing the remaining genetic material to flush down the artery. Perforated balloons are balloons which have small holes in them, typically formed by lasers. In use, fluid containing the genetic material is expelled through the holes in the balloons and into contact with the endothelial cells in the artery. These gene delivery systems however, have been compromised by issues relating to efficacy and/or safety.

Certain liabilities, however, inherent in the use of double-balloon and porous balloon catheters have been identified. For example, neither double-balloon nor porous balloon catheters can be used to perform the angioplasty itself. Thus, in those applications requiring both angioplasty and drug delivery, e.g., to inhibit restenosis, two procedures must be preformed. Additionally, the double balloon typically requires long incubation times of 20–30 min., while the high-velocity jets responsible for transmural drug delivery from the porous balloon catheter have been associated with arterial perforation and/or extensive inflammatory infiltration (Wolinsky, et al., J. Am. Coil. Cardiol., 15:475–481 (1990).

SUMMARY OF THE INVENTION

It has now been discovered that nucleic acids can be delivered to cells of an artery or blood vessel by contacting the cells with a hydrophilic polymer incorporating the nucleic acid, thus avoiding the use of a double-balloon or porous balloon catheter and the problems associated with such delivery systems. It has also been demonstrated that, unexpectedly, the percentage of transduced arterial cells is significantly higher using the present invention compared with use of a double-balloon catheter.

By "arterial cells" is meant the cells commonly found in mammalian arteries, including endothelial cells, smooth muscle cells, connective tissue cells and other cells commonly found in the arterial structure.

By "nucleic acid" is meant DNA and RNA, including antisense DNA or RNA.

It has further been discovered that a DNA encoding an angiogenic protein (a protein capable of inducing angiogenesis, i.e., the formation of new blood vessels), delivered by the method of the present invention is expressed by the arterial cell and induces angiogenesis in tissues perfused by the treated blood vessels. This allows for the treatment of diseases associated with vascular occlusion in a variety of target tissues, such as limb ischemia, ischemic cardiomyopathy, myocardial ischemia, cerebral ischemia and portal hypertension.

The present invention provides a method for the delivery of a nucleic acid to an arterial cell comprising contacting the cell with a hydrophilic polymer incorporating the nucleic acid. The nucleic acid may be any nucleic acid, DNA and RNA, including antisense DNA or RNA. The DNA may encode hormones, enzymes, receptors or drugs of interest. The nucleic acid is selected based upon the desired therapeutic outcome. For example, in the treatment of ischemic diseases, the genetic material of choice is DNA encoding an angiogenic protein. The nucleic acid may be carried by a microdelivery vehicle such as cationic liposomes and adenoviral vectors. DNA encoding different proteins may be used separately or simultaneously.

The hydrophilic polymer is selected to allow incorporation of the nucleic acid to be delivered to the arterial cell and its release when the hydrophilic polymer contacts the arterial cell. Preferably, the hydrophilic polymer is a hydrogel polymer. Other hydrophilic polymers will work, so long as they can retain the genetic material of the present invention, so that, on contact with arterial cells, transfer of genetic material occurs.

Suitable hydrogel polymers include, for example, those selected from the group consisting of polycarboxylic acids, cellulosic polymers, gelatin, polyvinylpyrrolidone, maleic anhydride polymers, polyamides, polyvinyl alcohols, and polyethylene oxides. The hydrogel polymer is preferably polyacrylic acid.

Without wishing to be bound by theory, one reason that the use of hydrogel, and particularly with hydrogel coated balloon catheters, is believed to provide improved results over, for example, prior treatments with double balloon catheters, is that the use of standard balloon catheters with hydrogel surfaces causes the hydrogel not only to contact the endothelial cells which line the interior of the arteries, but also displaces the endothelial cells sufficiently to permit contact between the hydrogel and the smooth muscle cells which underlie the endothelial cell layer. This permits expression of polypeptides in different arterial cell types, which enhances the kinds and amounts of therapeutic polypeptides which can be produced in accordance with this invention. For example, as indicated in the examples below, the present method successfully produces sufficient amounts of vascular endothelial growth factor (VEGF) to cause angiogenesis downstream from a DNA/arterial contact point, despite the fact that VEGF is not normally produced even by transformed endothelial cells, but is produced by smooth muscle cells of the type that surround the endothelial cells in the artery.

The arterial cell may be contacted with the hydrophilic polymer incorporating the DNA by means of an applicator such as a catheter which is coated with the DNA-bearing hydrophilic polymer. Preferably, the applicator can exert some pressure against the arterial cells, to improve contact between the nucleic acid-bearing hydrophilic polymer and the arterial cells. Thus a balloon catheter is preferred. Preferably, the hydrophilic polymer coats at least a portion of an inflatable balloon of the balloon catheter.

The present invention further includes compositions comprising hydrophilic polymers incorporating nucleic acid. Preferably the hydrophilic polymer is a hydrogel and the nucleic acid is DNA which encodes an angiogenic protein.

The present invention also provides kits for application of genetic material to the interior of an artery or similar bodily cavity, comprising a substrate, such as a catheter or a suitably shaped rod, and a source of genetic material comprising the DNA coding for the desired therapeutic polypeptide. Preferably, the present invention is directed to a catheter adapted for insertion into a blood vessel, having a balloon element adapted to be inserted into the vessel and expandable against the walls of the vessel. At least a portion of the balloon element is defined by a coating of a hydrophilic polymer, and incorporated within the hydrophilic polymer coating, a nucleic acid to be delivered to the arterial cell. The hydrophilic polymer is preferably a hydrogel polymer, most preferably a hydrophilic polyacrylic acid polymer.

The present invention also provides a method for inducing angiogenesis in a desired target tissue, comprising delivering a DNA encoding an angiogenic protein to an arterial cell in an artery or blood vessel perfusing the target tissue.

Other aspects of the invention are discussed infra.

As used herein the term "angiogenic protein" means any protein, polypeptide, mutein or portion thereof that is capable of inducing the formation of new blood vessels. Such proteins include, for example, acidic and basic fibroblast growth factors (aFGF and bFGF), vascular endothelial growth factor (VEGF), epidermal growth factor (EGF), transforming growth factor $\alpha$ and $\beta$ (TGF-$\alpha$ and TFG-$\beta$), platelet-derived endothelial growth factor (PD-ECGF), platelet-derived growth factor (PDGF), tumor necrosis factor $\alpha$ (TNF-$\alpha$), hepatocyte growth factor (HGF) and insulin like growth factor. Preferably, the angiogenic protein contains a secretory signal sequence allowing for secretion of the protein from the arterial cell. VEGF is a preferred protein.

BRIEF DESCRIPTION OF THE DRAWINGS

FIG. 1(a) is a representative angiogram recorded 10 days after surgery. Once the femoral artery is excised, thrombotic occlusion of the external lilac artery extends retrograde to its origin from the common lilac (arrow). Open arrow indicates the site of arterial gene transfer. In FIG. 1(b) the shaded segment of femoral artery has been excised.

In FIGS. 2(a) and 2(b) the expression of the human VEGF mRNA was evident in the rabbit lilac artery (lane 4) and cultured rabbit vascular smooth muscle cells (lane 6, positive control) which were transfected with human VEGF gene. Arrows indicate position of VEGF band at 258 bp. Lane 1 depicts the results using a molecular weight marker, namely pGEM3zf(-) digested with Hae III; lane 2 is a negative control (no RNA); lane 3 is a second negative control (rabbit lilac artery transfected with $\beta$-galactosidase expression plasmid); and lane 5 is a further negative control (PCR analysis of the VEGF-transfected lilac artery excluding the reverse transcriptase reaction). FIG. 2(c) shows the nucleotide sequence of the RT-PCR product from a transfected rabbit lilac artery. Direct sequencing of the 258 bp bands obtained by RT-PCR confirmed that this band represented the human VEGF sequence. The sequence designated in 2(c) corresponds to amino acids 69 to 75 of the VEGF peptide. Asterisks denote the nucleotides which are not conserved among different species of the VEGF gene (rat, mouse, bovine, guinea pig) demonstrating that the exogenous human gene was amplified by the RT-PCR procedure.

FIG. 4(a) the angiographic score at day 0 (immediately prior to transfection), and days 10 and 30 post-transfection. FIG. 4(b) Calf Blood pressure ratio at day 0, and at days 10 and 30 post-transfection. FIG. 4(c) depicts capillary density at day 30 post-transfection. (*p<0.05, **p<0.01)

FIG. 5(a) depicts the muscle of an animal transfected with pGSVLacZ. FIG. 5(b) depicts the muscle of an animal transfected with phVEGF$_{165}$. The dark staining indicates capillaries as shown by the arrows.

DETAILED DESCRIPTION OF THE INVENTION

The present invention provides a method for the delivery of nucleic acid to an arterial cell comprising contacting the cell with a hydrophilic polymer incorporating the nucleic acid.

The nucleic acid may be any nucleic acid which when introduced to the arterial cells provides a therapeutic effect. The nucleic acid is selected based upon the desired therapeutic outcome. For example, in the treatment of ischemic diseases, one genetic material of choice would be a DNA encoding an angiogenic protein. DNA useful in the present invention include those that encode hormones, enzymes, receptors or drugs of interest. The DNA can include genes encoding polypeptides either absent, produced in diminished quantities, or produced in mutant form in individuals suffering from a genetic disease. Additionally it is of interest to use DNA encoding polypeptides for secretion from the target cell so as to provide for a systemic effect by the protein encoded by the DNA. Specific DNA's of interest include those encoding hemoglobin, interleukin-1, interleukin-2, interleukin-3, interleukin-4, interleukin-4, interleukin-5, interleukin-6, interleukin-7, interleukin-8, interleukin-9, interleukin-10, interleukin-11, etc., GM-CSF, G-CSF, M-CSR, human growth factor, insulin, factor VIII, factor IX, tPA, LDL receptors, tumor necrosis factor, PDGF, EGF, NGF, IL-1ra, EPO, β-globin and the like, as well as biologically active muteins of these proteins. The nucleic acid utilized may also be "anti-sense" DNA or RNA, which binds to DNA or RNA and blocks the production of harmful molecules. In addition, the DNA carried to the arterial cells in accordance with the present invention may code for polypeptides which prevent the replication of harmful viruses or block the production of smooth muscle cells in arterial walls to prevent restenosis.

Antisense RNA molecules are known to be useful for regulating translation within the cell. Antisense RNA molecules can be produced from the corresponding gene sequences. The antisense molecules can be used as a therapeutic to regulate gene expression associated with a particular disease.

The antisense molecules are obtained from a nucleotide sequence by reversing the orientation of the coding region with regard to the promoter. Thus, the antisense RNA is complementary to the corresponding mRNA. For a review of antisense design see Green, et al., *Ann. Rev. Biochem.* 55:569–597 (1986), which is hereby incorporated by reference. The antisense sequences can contain modified sugar phosphate backbones to increase stability and make them less sensitive to RNase activity. Examples of the modifications are described by Rossi, et al., *Pharmacol, Ther.* 50(2):245–354, (1991).

In certain therapeutic applications, such as in the treatment of ischemic diseases, it may be desirable to induce angiogenesis, i.e., the formation of new blood vessels. For such applications, DNA's encoding growth factors, polypeptides or proteins, capable of inducing angiogenesis are selected. Folkman, et al., *Science,* 235:442–447 (1987). These include, for example, acidic and basic fibroblast growth factors (aFGF and bFGF), vascular endothelial growth factor (VEGF), epidermal growth factor (EGF), transforming growth factor α and β (TGF-β and TGF-β), platelet-derived endothelial cell growth factor (PD-ECGF), platelet-derived growth factor (PDGF) itself, tumor necrosis factor α (TNF-α), hepatocyte growth factor (HGF) and insulin like growth factor. See, Klagsbrun, et al., *Annu. Rev. Physiol.,* 53:217–239 (1991) and Folkman, et al., *J. Biol. Chem.* 267:10931–10934 (1992). Muteins or fragments of an angiogenic protein may be used as long as they induce or promote the formation of new blood vessels.

Recent investigations have established the feasibility of using recombinant formulations of such angiogenic growth factors to expedite and/or augment collateral artery development in animal models of myocardial and hindlimb ischemia. See, Baffour, et al., *J. Vasc. Surg.,* 16:181–191 (1992) (bFGF); Pu, et al, *Circulation,* 88:208–215 (1993) (aFGF); Yanagisawa-Miwa, et al., *Science,* 257:1401–1403 (1992) (bFGF); Ferrara, et al., *Biochem. Biophys. Res. Commun.,* 161:851–855 (1989) (VEGF).

VEGF was also purified independently as a tumor-secreted factor that included vascular permeability by the Miles assay (Keck, et al, *Science,* 246:1309–1342 (1989) and Connolly, et al., *J. Biol Chem.,* 264:20017–20024 (1989)), and thus its alternate designation, vascular permeability factor (VPF). VEGF is a preferred angiogenic protein. Two features distinguish VEGF from other heparin-binding, angiogenic growth factors. First, the $NH_2$ terminus of VEGF is preceded by a typical signal sequence; therefore, unlike bFGF, VEGF can be secreted by intact cells. Second, its high-affinity binding sites, shown to include the tyrosine kinase receptors Flt-1 and Flt-1/KDR are present on endothelial cells. Ferrara, et al., *Biochem. Biophys. Res. Commun.,* 161:851–855 (1989) and Conn, et al., *Proc. Natl. Acad. Sci. USA,* 87:1323–1327 (1990). (Interaction of VEGF with lower affinity binding sites has been shown to induce mononuclear phagocyte chemotaxis). Shen, et al., *Blood,* 81:2767–2773 (1993) and Clauss, et al., *J. Exp. Med.,* 172:1535–1545 (1990).

Evidence that VEGF stimulates angiogenesis in vivo had been developed in experiments performed on rat and rabbit cornea (Levy, et al., *Growth Factors,* 2:9–19 (1989) and Connolly, et al., *J. Clin. Invest.,* 84:1470–1478 (1989)), the chorioallantoic membrane (Ferrara, et al., Biochem Biophys Res Commun., 161:851–855 (1989)), and the rabbit bone graft model. Connolly, et al., *J. Clin. Invest.,* 84:1470–1478 (1989).

Preferably, the angiogenic protein contains a secretory signal sequence that facilitates secretion of the protein from the arterial cell. Angiogenic proteins having native signal sequences, e.g., VEGF, are preferred. Angiogenic proteins that do not have native signal sequences, e.g., bFGF, can be modified to contain such sequences using routine genetic manipulation techniques. See, Nabel et al., *Nature* 362:844 (1993).

The nucleotide sequence of numerous peptides and proteins, including angiogenic proteins, are readily available through a number of computer data bases, for example, GenBank, EMBL and Swiss-Prot. Using this information, a DNA segment encoding the desired may be chemically synthesized or, alternatively, such a DNA segment may be obtained using routine procedures in the art, e.g, PCR amplification.

To simplify the manipulation and handling of the DNA, prior to introduction to the arterial cell, the DNA is preferably inserted into a vector, e.g., a plasmid vector such as pUC118, pBR322, or other known plasmid vectors, that includes, for example, an *E. Coli* origin of replication. See, Sambrook, et al., *Molecular Cloning:A Laboratory Manual,* Cold Spring Harbor Laboratory press, (1989). The plasmid vector may also include a selectable marker such as the β-lactamase gene for ampicillin resistance, provided that the marker polypeptide does not adversely effect the metabolism of the organism being treated. Additionally, if necessary, the DNA may be operably linked to a promoter/enhancer region capable of driving expression of the protein in the arterial cell. An example of a suitable promoter is the 763-base-pair cytomegalovirus (CMV) promoter. Normally, an enhancer is not necessary when the CMV promoter is used. The RSV and MMT promoters may also be used. Certain proteins can expressed using their native promoter.

If desired, the DNA may be used with a microdelivery vehicle such as cationic liposomes and adenoviral vectors. For a review of the procedures for liposome preparation, targeting and delivery of contents, see Mannino and Gould-Fogerite, *Bio Techniques,* 6:682 (1988). See also, Felgner and Holm, *Bethesda Res. Lab. Focus,* 11(2):21 (1989) and Maurer, R. A., *Bethesda Res. Lab. Focus,* 11(2):25 (1989). Replication-defective recombinant adenoviral vectors, can be produced in accordance with known techniques. See, Quantin, et al., *Proc. Natl. Acad. Sci. USA,* 89:2581–2584 (1992); Stratford-Perricadet, et al., *J. Clin. Invest.,* 90:626–630 (1992); and Rosenfeld, et al., *Cell,* 68:143–155 (1992).

In certain situations, it may be desirable to use DNA's encoding two or more different proteins in order optimize the therapeutic outcome. For example, DNA encoding two angiogenic proteins, e.g., VEGF and bFGF, can be used, and provides an improvement over the use of bFGF alone. Or an angiogenic factor can be combined with other genes or their encoded gene products to enhance the activity of targeted cells, while simultaneously inducing angiogenesis, including, for example, nitric oxide synthase, L-argine, fibronectin, urokinase, plasminogen activator and heparin.

The hydrophilic polymer is selected to allow incorporation of the DNA to be delivered to the arterial cell and its release when the hydrophilic polymer contacts the arterial cell.

Preferably, the hydrophilic polymer is a hydrogel polymer, a cross-linked polymer material formed from the combination of a colloid and water. Cross-linking reduces solubility and produces a jelly-like polymer that is characterized by the ability to swell and absorb liquid, e.g., that containing the DNA. Suitable hydrogel polymers include, for example, those selected from the group consisting of polycarboxylic acids, cellulosic polymers, gelatin, polyvinylpyrrolidone, maleic anhydride polymers, polyamides, polyvinyl alcohols, and polyethylene oxides. Preferred hydrogels are polyacrylic acid polymers available as HYDROPLUS (Mansfield Boston Scientific Corp., Watertown, Mass.) and described in U.S. Pat. No. 5,091,205.

The nucleic acid in aqueous solution is incorporated into the hydrophilic polymer to form a nucleic acid-hydrophilic polymer composition. The nucleic acid is incorporated without complexing or chemical reaction with the hydrophilic polymer, and is preferably relatively freely released therefrom when placed in contact with the arterial cells. The resulting structure comprises a support, e.g. the balloon of the balloon catheter, on which is mounted the hydrogel, in or on which is incorporated the desired DNA and its associated vehicle, e.g., phage or plasmid vector. The hydrophilic polymer is preferably adhered to the support, so that after application of the DNA to the target cells, the hydrophilic polymer is removed with the support.

An arterial cell is contacted with the nucleic acid-hydrophilic polymer composition by any means familiar to the skilled artisan. The preferred means is a balloon catheter having the hydrophilic polymer on its outer surface, which permits the contact between the hydrophilic polymer bearing the nucleic acid to be transferred and the arterial cells to be made with some pressure, thus facilitating the transfer of the nucleic acid to the cells. However, other supports for the hydrophilic polymer are also useful, such as catheters or solid rods having a surface of hydrophilic polymer. Preferably, the catheters or rods or other substrates which are flexible, to facilitate threading through the arteries to reach the point of intended application. For cells that are not in tubular arteries, other types of catheters, rods or needles may be used.

When a hydrophillic arterial balloon is used, it is not necessary to protect the balloon prior to inflation, since relatively little of the nucleic acid is lost in transit to the treatment site until the balloon is inflated and the hydrophilic polymer bearing the nucleic acid is pressed against the arterial cells. When hydrophilic polymer-surfaced catheters or rods are used as the vehicle or substrate, the surface can protected, e.g. by a sheath, until the point of intended application is reached, and then the protection removed to permit the hydrophilic polymer bearing the nucleic acid to contact the arterial cells.

The vehicle, be it arterial balloon, catheter, flexible rod or other shaped vehicle, can be furnished with means to assist in accurate placement within the intended body cavity. For example, it can be furnished with a radioactive element, or made radio-opaque, furnished with means permitting easy location using ultrasound, etc.

Preferably, the nucleic acid-hydrophilic composition contacts the arterial cell by means of a catheter. The catheter is preferably a balloon catheter constructed for insertion in a blood vessel and has a catheter shaft and an expandable dilation balloon mounted on the catheter shaft. At least a portion of the exterior surface of the expandable portion is defined by a coating of a tenaciously adhered hydrophilic. Incorporated in the hydrophilic polymer is an aqueous solution of the DNA to be delivered to the arterial cells.

In general, when dry, the hydrophilic polymer (preferably hydrogel) coating is preferably on the order of about 1 to 10 microns thick, with a 2 to 5 micron coating typical. Very thin hydrogel coatings, e.g., of about 0.2–0.3 microns (dry) and much thicker hydrogel coatings, e.g., more than 10 microns (dry), are also possible. Typically, hydrogel coating thickness may swell by about a factor of 2 to 10 or more when the hydrogel coating is hydrated.

Procedures for preparing a balloon with a hydrogel coating are set forth in U.S. Pat. No. 5,304,121, the disclosure of which is incorporated herein by reference.

Figure 6:
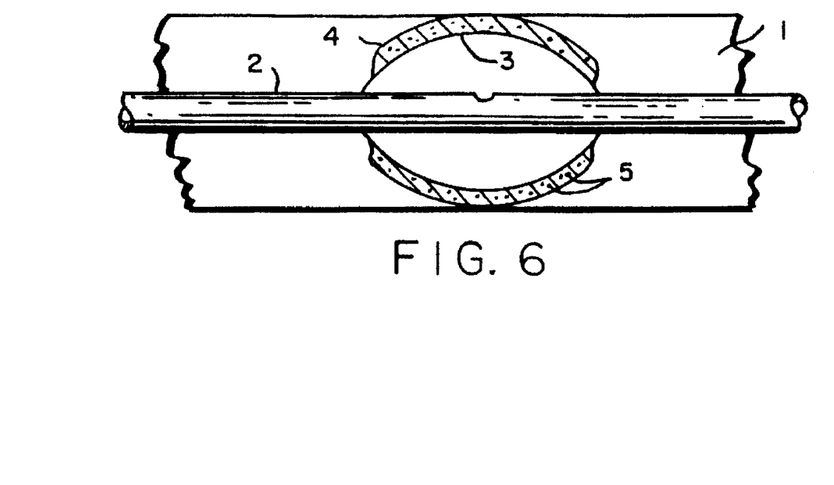
FIG. 6 illustrates a diagrammatical cross section of a balloon catheter having a hydrophilic surface bearing genetic material in accordance with the present invention, in place within an artery.

A representative catheter is set forth in FIG. 6. Referring to FIG. 6, 1 is the wall of the blood vessel. The figure shows the catheter body 2 held in place by the inflation of an inflation balloon 3. The balloon comprises a hydrogel coating 4 incorporating DNA 5.

In use, the DNA, for example, is applied ex vivo to the hydrophilic polymer coating of the balloon. To facilitate application, the balloon may be inflated. If necessary, the polymer may be dried with warm air and the DNA application repeated. The amount of DNA to be applied to the arterial surface depends on the purpose of the DNA and the ability of the DNA to be expressed in the arterial cells. Generally, the amount of naked DNA applied to the balloon catheter is between about 0.1 and 100 $\mu g/mm^2$, more preferably between about 0.5 and about 20 $\mu g/mm^2$, most preferably between about 1.5 and about 8 $\mu g/mm^2$. Preferably, between 0.5 mg and 5 mg of DNA are applied to the hydrogel coating of a balloon catheter having an inflated lateral area of about 630 $mm^2$ (e.g., a balloon catheter having an inflated diameter of about 5 mm and a length of about 40 mm), providing a surface having about 0.8 to about 8 $\mu g/mm^2$ of DNA when the balloon is inflated and contacts the interior of the artery. More preferably, between 1 mg and 3 mg of DNA are applied to the polymer, providing a DNA loading of about 1.6 to about 4.8 $\mu g/mm^2$.

The catheter is inserted using standard percutaneous application techniques and directed to the desired location, e.g., an artery perfusing the target tissue. For example, in the treatment of patients with occlusive peripheral arterial disease (PAD), the balloon is directed towards an artery of the leg, e.g., lilac. Once the balloon has reached its desired location, it is inflated such that the hydrogel coating of the balloon contacts the arterial cells located on the walls of the artery and remains inflated for a time sufficient to allow transfer of the DNA encoding the angiogenic protein from the hydrogel to the arterial cells. Preferred periods of balloon inflation range from 30 seconds to 30 minutes, more preferably 1 minute to 5 minutes. Surprisingly, that is normally sufficient time to permit transfer of the DNA by the method of the present invention.

Once transferred, the DNA coding for the desired therapeutic polypeptide is expressed by the arterial cells for a period of time sufficient for treatment of the condition of interest. Because the vectors containing the DNA of interest are not normally incorporated into the genome of the cells, however, expression of the protein of interest takes place for only a limited time. Typically, the therapeutic protein is only expressed in therapeutic levels for about two days to several weeks, preferably for about 1–2 weeks. Reapplication of the DNA can be utilized to provide additional periods of expression of the therapeutic polypeptide. If desired, use of a retrovirus vector to incorporate the heterologous DNA into the genome of the arterial cells will increase the length of time during which the therapeutic polypeptide is expressed, from several weeks to indefinitely.

In one preferred application, the DNA-hydrogel polymer composition can be used to deliver a DNA encoding an angiogenic protein to an arterial cell in an artery or blood vessel perfusing the target tissue. Expression of the angiogenic protein and its secretion from the arterial cell induces angiogenesis, i.e., the formation of new blood vessels, in target tissues perfused by the artery or blood vessels, allowing for the treatment of diseases associated with vascular occlusion such as limb ischemia, ischemic cardiomyopathy, myocardial ischemia, cerebral ischemia and portal hypertension.

The present invention makes genetic treatment possible which can correct heretofore incorrectable problems.

The present invention is further illustrated by the following examples. These examples are provided to aid in the understanding of the invention and are not construed as a limitation thereof.

EXAMPLE 1

Direct Gene Transfer with Hydrogel Polymer Balloon Catheter Applied to an Angioplasty Catheter Balloon Can be Used to Effect Direct Gene Transfer to the Arterial Wall.

DNA solution was applied to the surface of an angioplasty catheter balloon with a hydrogel polymer (marketed under the mark Slider™ with Hydroplus® by Mansfield Boston Scientific Corp., Watertown, Mass.). The catheter was constructed with a single polyethylene balloon, 2.0 mm in diameter and 2.0 cm in length. The Hydroplus® coating consists of a hydrophilic polyacrylic acid polymer, crosslinked via an isocyanate onto the balloon to form an ultra-high molecular weight hydrogel with tight adherence to the balloon surface. The thickness of the hydrogel coating when dry measures between 3–5 μm; upon exposure to an aqueous environment, the coating swells to 2–3 times its initially dry thickness. In order to apply DNA to the catheter, the balloon was inflated to 4 atm, following which 20 μl of DNA solution were pipetted and distributed onto the balloon surface using a sterile pipette tip. After the balloon's hydrogel polymer was covered with a homogeneous film of DNA solution, the hydrogel was dried with warm air. The above procedure was then repeated, resulting in a total of 40 μl of DNA solution applied to the balloon.

For percutaneous application, luciferase DNA concentration was 3.27 μg/μl. DNA was dissolved in TE buffer (10 mM Tris, 1 mM EDTA).

(Attempts were made to apply DNA solution to standard uncoated balloons as well. The hydrophobic surface of the polyethylene balloon, however, made it impossible to cover the balloon with a film of DNA solution.)

To determine the total amount of DNA which is successfully absorbed onto the balloon surface, 5 hydrogel balloons were coated with 40 μl DNA (2 μg DNA/μl) containing a small amount of $^{35}$S-labeled luciferase plasmid. (Levy, et al., Growth Factors, 2:1535–1545 (1990)). A random primed DNA labeling kit (United States Biochemical, Cleveland, Ohio) was used for the labeling reaction an unincorporated nucleotides were remove by ethanol precipitation. After the coating procedure, the catheter tip was placed in 0.5 ml water for 15 minutes at room temperature, and 1.0 ml gel solubilizer (Solvable,™ New England Nuclear, Boston, Mass.) for 3 hours at 50° C. to dissolve the gel before the scintillation fluid was added. The amount of DNA on the balloon was calculated from the quotient: [counts per minute (cpm) in a scintillation vial containing the balloon]/[cpm in a vial containing 40 μl of the same lot of labeled DNA (80 μg)]. Scintillation counts were corrected for quench and chemiluminescence.

After coating hydrogel balloons with 40 μl of DNA solution (containing 80 μg of radiolabeled DNA), and drying the gel, the magnitude of DNA retained on the hydrogel balloon was determined by comparing the amount of radioactivity on the balloons to the amount of radioactivity in 40 μl of the original radiolabeled DNA solution. Scintillation counting revealed that 97±2% (n=5) of the radioactively labeled DNA remained on the hydrogel coated balloon, corresponding to 78±1.5 μg of luciferase DNA.

Reporter Genes

The firefly luciferase gene and the gene for nuclear-specific β-galactosidase (β-gal) were used as reporter genes to monitor the results of the transfection procedures. The luciferase expression vector, pRSVLUC (courtesy of Dr. Allen Brasier, Massachusetts General Hospital, Boston, Mass.), consist of a full length Photinus pyralis luciferase cDNA (pJD 204) (de Wet et al., 1987) inserted into a PGEM3-plasmid (Brasier et al. Biotechniques, 7:1116–1122 (1989)), under the control of Rous sarcoma virus long terminal repeat (RSV-LTR) promoter. The pGSVLacZ vector contains the simian virus (SV40) large tumor nuclear location signal fused to the lacZ gene (nls β-gal) (Bonnerot et al., Proc. Natl. Acad. Sci. U.S.A., 84:6795–6799 (1987)) (gift from Dr. Claire Bonnerot, Institut Pasteur, Paris, France), inserted into a pGEM1-plasmid. Nuclear staining identifies the exogenous construct designed to permit nuclear translocation, and thus distinguishes expression of the transgene from endogenous (cytoplasmic) β-gal activity. Previous concerns (Lim et al., Circulation, 83:2007–2011 (1991)) regarding nonspecificity of blue staining resulting from β-gal are thus eliminated.

Analysis of Luciferase Activity

The magnitude of gene expression was determined by measuring luciferase activity as described previously (Leclerc et al., J. Clin. Invest., 90:936–944 (1992)) using the Luciferase Assay System (Promega, Madison, Wis.). Briefly, frozen arteries were homogenized and dissolved in 300 μl of Cell Culture Lysis Reagent (Promega) containing 1 mg/ml bovine serum albumin. Three different 20-μl aliquots prepared from each transfected specimen were mixed in a sample tube with 100 μl of Luciferase Assay Reagent (Promega, Madison, Wis.) and inserted into a luminometer (Model 20e, Turner Design, Sunnyvale, Calif.) that reports results on a scale established to yield as low as $10^{-3}$ Turner light units (TLU). The specimen's total luciferase activity was calculated from the mean of the three aliquots analyzed. The luciferase values were in the linear range of a standard curve derived from samples with a known amount of luciferase (Sigma, St. Louis, Mo., catalogue #L9009). The lyophilized luciferase was, according to the manufacturer's instructions, dissolved in sterile water and further diluted in Cell Culture Lysis Reagent with 1 mg/ml bovine serum albumin. The following equation was used to convert TLU into pg luciferase: Luciferase [pg]=−0.08+0.051 TLU. Using this formula, 100 TLU corresponds to 5.0 pg of luciferase. It must be noted that the specific activity of luciferase standards from different vendors can vary considerably (Wolff, et al., *Biotechniques*, 11:474–485 (1991)); therefore, direct comparisons of luciferase reported by different groups must be made with caution, especially when the origin of the standard used is not specified.

Percutaneous Transfection

Percutaneous gene transfer experiments with the luciferase gene were performed in 13 rabbits using a catheter with a balloon to which a 20 μm hydrogel coating had been applied and which was advanced through a 5 F teflon sheath. The balloon was advanced beyond the distal tip of the sheath, coated with 130 μg luciferase DNA, and pulled back into the sheath to protect the balloon from subsequent contact with blood. The sheath and the angioplasty catheter were then introduced via the right carotid artery and advanced to the left common lilac artery under fluoroscopic control. The balloon catheter was advanced 2 cm further (beyond the distal sheath tip) into the external lilac artery and inflated there for 1 or 5 min. Following balloon deflation, the catheter system was removed. In 10 animals, the transfected external lilac artery as well as the contralateral control artery were removed 3 days later, weighed, and assayed for luciferase activity. In 3 additional animals, which had been transfected for 5 min. only, the arteries were excised 14 days after gene transfer. In these 3 animals we also removed the left femoral artery to check for luciferase expression directly downstream of the transfected segment.

Results

Luciferase expression was detected in all 10 (100%) percutaneously transfected arteries excised after 3 days, whether inflated for 5 min (386±299 TLU, n=5) or 1 min (113±59 TLU, n=5).

Three additional animals, in which balloons were inflated for 5 min only, were sacrificed after 14 days. Individual luciferase expression was 152.6, and 16 TLU, respectively (mean=58±47 TLU). In this series, we also measured luciferase in the adjacent femoral artery, which was not inflated. Luciferase expression in all these arteries was undistinguishable from background activity (mean 0.04±0.29 TLU).

The findings demonstrate that endoluminal vascular gene transfer can be achieved successfully and consistently with pure DNA applied to a standard angioplasty catheter balloon coated with hydrogel polymer. The hydrogel provides the absorbable medium to which one may apply a solution of pure DNA. Drying of the gel results in a layer of concentrated DNA which is then transferred to the arterial wall as the balloon contacts the arterial wall coincident with balloon inflation. Experiments with radiolabeled DNA established that 97% of DNA applied in aqueous solution to the hydrogel-coated balloon was still present on the balloon after drying of the gel. Autoradiograms of the arterial wall demonstrated that inflation of the hydrogel balloon results in DNA uptake which is distributed across the full thickness of the arterial wall. DNA was shown to penetrate the intact internal elastic lamina and was distributed intracellularly as well as extracellularly.

Despite elimination of accessory transfection vehicles in this example, both the frequency of successful transfection and the magnitude of reporter gene expression achieved were superior to that previously reported from our laboratory (Leclerc, et al., *J. Clin Invest.*, 90:936–944 (1992)) and comparable to the results achieved by others (Chapman, et al., *Circ. Res.*, 71:27–33 (1992) and Lim, et al., *Circulation*, 83:2007–2011 (1991)) using alternative delivery schemes. The success rate of transfection in our rabbit model as measured by expression of the luciferase transgene was 100% (37 of 37 artery segments), even in those cases in which the inflation time was reduced to one minute. The duration of inflation within a range from 10 to 30 minutes did not have significant impact on transfection efficiency, a feature which would be expected to facilitate human arterial, particularly coronary, gene transfer.

EXAMPLE 2

Induction of Angiogeneses In Vivo

Methods

Figure 1A:
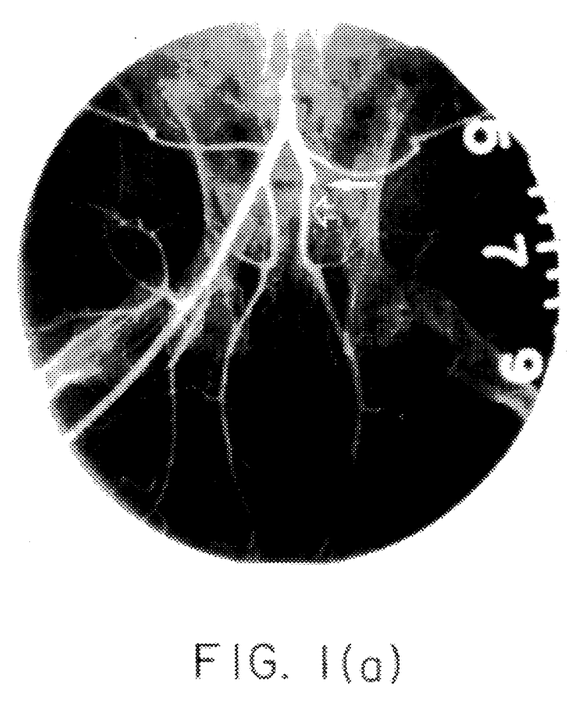
FIGS. 1(a) and 1(b) show the rabbit ischemic hindlimb model.
Figure 1B:
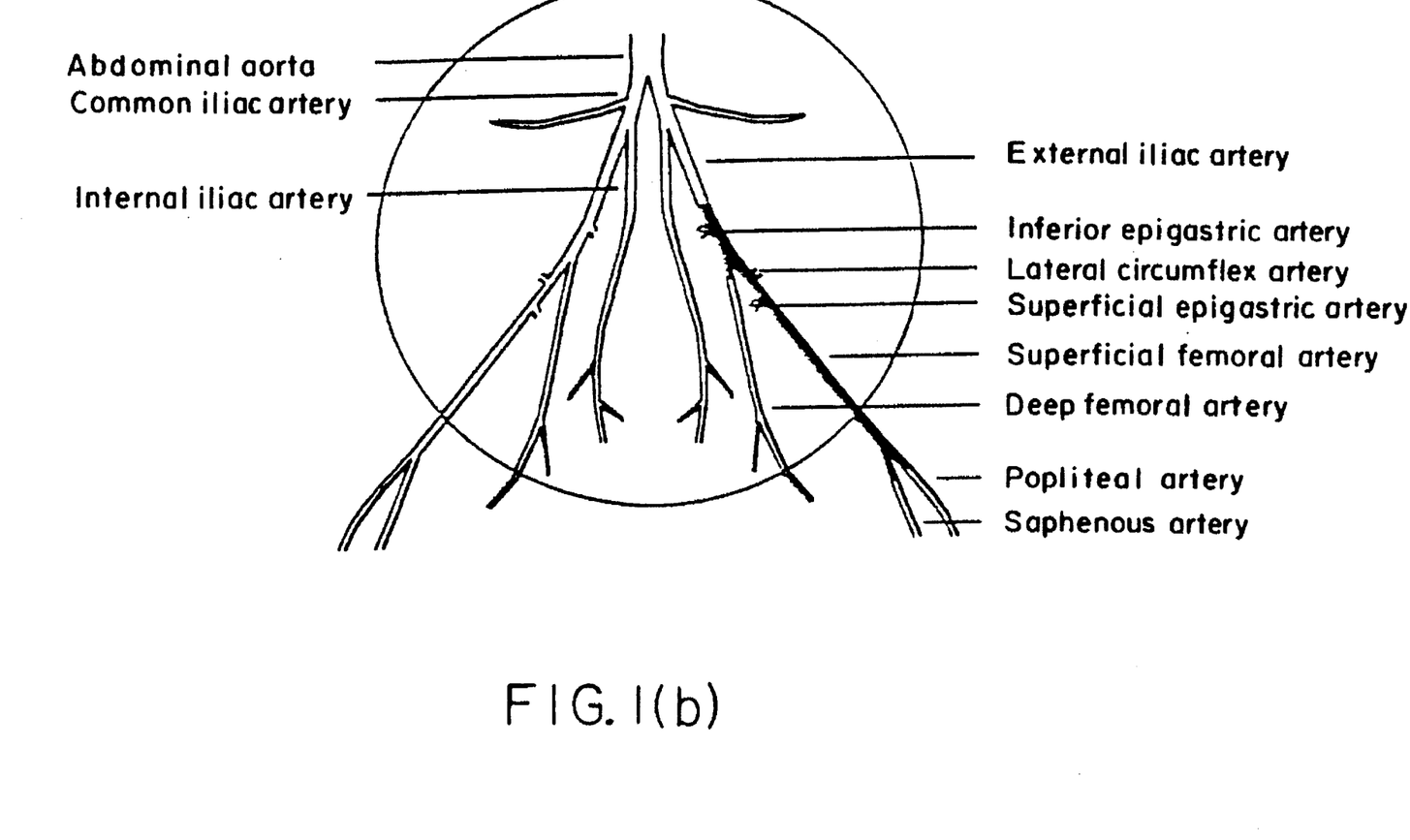

Animal Model (FIG. 1).

The angiogenic response to transfection of the gene for vascular endothelial growth factor (VEGF) was investigated using a rabbit ischemic hindlimb model. Takeshita, et al., *J. Clin. Invest.*, 93:662–670 (1994) and Pu, et al., *J. Invest Surg.*, (In Press). All protocols were approved by St. Elizabeth's Institutional Animal Care and Use Committee. Male New Zealand White rabbits weighing 4–4.5 kg (Pine Acre Rabbitry, Norton, Mass.) were anesthetized with a mixture of ketamine (50 mg/kg) and acepromazine (0.8 mg/kg) following premedication with xyazine (2.5 mg/kg). A longitudinal incision was then performed, extending inferiorly from the inguinal ligament to a point just proximal to the patella. The limb in which the incision was performed— right versus left—was determined at random at the time of surgery by the surgeon. Through this incision, using surgical loops, the femoral artery was dissected free along its entire length; all branches of the femoral artery, including the inferior epigastric, deep femoral, lateral circumflex and superficial epigastric arteries, were also dissected free. After further dissecting the popliteal and saphenous arteries distally, the external lilac artery as well as all of the above arteries were ligated. Finally, the femoral artery was completely excised from its proximal origin as a branch of the external lilac artery, to the point distally where it bifurcates into the saphenous and popliteal arteries. Once the femoral artery is excised, thrombotic occlusion of the external lilac artery extends retrograde to its origin from the common lilac (FIG. 1(a), arrow). As a result, the blood supply to the distal limb is dependent on the collateral arteries which may originate from the internal lilac artery. Accordingly, direct arterial gene transfer of VEGF was performed in to the internal lilac artery of the ischemic limb. Post-operatively, all animals were closely monitored. Analgesia (levorphanol tartrate 60 mg/kg, Roche Laboratories, Nutley, N.J.) was administered subcutaneously as required for evidence of discomfort throughout the duration of the experiment. Prophylactic antibiotics (enrofloxacin 2.5 mg/kg, Miles, Shawnee Mission, Kans.) was also administered subcutaneously for a total of 5 days post-operatively.

Plasmids and Smooth Muscle Cell (SMC) Transfection in Vitro.

Complementary DNA clones for recombinant human VEGF$_{165}$, isolated from cDNA libraries prepared from HL60 leukemia cells, were assembled into a mammalian expression vector containing the cytomegalovirus promoter. Leung, et al., *Science*, 246:1306–1309 (1989). The biological activity of VEGF$_{165}$ secreted from cells transfected with this construct (phVEGF$_{165}$) was previously confirmed by the evidence that media conditioned by transfected human 293 cells promoted the proliferation of capillary cells. Leung, et al., *Science*, 246:1306–1309 (1989).

To evaluate expression of phVEGF$_{165}$ in vascular cells, rabbit arterial smooth muscle cells (SMCs) were transfected in vitro. Cells were cultured by explant outgrowth from the thoracic aorta of New Zealand White rabbits. The identity of vascular SMCs was confirmed morphologically using phase contrast microscopy and by positive immunostaining using a monoclonal antibody to smooth muscle α-actin (Clone 1A4, Sigma, St. Louis, Mo.). Cells were grown in the media (M199, GIBCO BRL, Gaithersberg, Md.) supplemented with 10% fetal bovine serum (FBD, GIBCO BRL). In vitro transfection was performed by incubating SMCs ($1.48 \times 10^6$ cells/10 cm plate) with 11.5 µg of the plasmid DNA and 70 µg of liposomes (Transfection-reagent, Boehringer Mannheim, Indianapolis, Ind.) as previously described. Pickering, et al., *Circulation*, 89:13–21 (1994). After completion of transfection, media was changed to 10% FBS. Culture supernatant was sampled at 3 days pot-transfection, and was analyzed by ELISA assay for VEGF protein. Houck, et al., *J. Biol. Chem.* 267:26031–26037 (1992).

The plasmid pGSVLacZ (courtesy of Dr. Claire Bonnerot) containing a nuclear targeted β-galactosidase sequence coupled to the simian virus 40 early promoter (Bonnerot, et al., *Proc. Natl. Acad. Sci. USA*, 84:6795–6799 (1987)) was used for all the control transfection experiments.

Percutaneous Arterial Gene Transfer in Vitro.

An interval of 10 days between the time of surgery and gene transfer was allowed for post-operative recovery of rabbits and development of endogenous collateral vessels. Beyond this time-point, studies performed up to 90 days post-operatively (Pu, et al., *J. Invest. Surg.*, (In Press)) have demonstrated no significant collateral vessel augmentation. At 10 days post-operatively (day 0), after performing a baseline angiogram (see below), the internal lilac artery of the ischemic limb of 8 animals was transferred with phVEGF$_{165}$ percutaneously using a 2.0 mm hydrogel-coated balloon catheter (Slider™ with HYDROPLUS.® Boston Scientific, Watertown, Mass.). The angioplasty balloon was prepared (ex vivo) by first advancing the deflated balloon through a 5 Fr. teflon sheath (Boston Scientific), applying 400 µg of phVEGF$_{165}$ to the 20 µm-thick later of hydrogel on the external surface of the inflated balloon, and then retracting the inflated balloon back into the protective sheath. The Sheath and angioplasty catheter were then introduced via the right carotid artery, and advanced to the lower abdominal aorta using a 0.014 inch guidewire (Hi-Torque Floppy II, Advanced Cardiovascular Systems, Temecula, Calif.) under fluoroscopic guidance. The balloon catheter was then advanced out of the sheath into the internal lilac artery of the ischemic limb, inflated for 1 min at 6 atmospheres, deflated, and withdrawn (FIG. 1(*a*), open arrow). An identical protocol was employed to transfect the internal iliac artery of 9 control animals with the plasmid pGSVLacZ containing a nuclear targeted β-galactosidase sequence. Heparin was not administered at the time of transfection or angiography.

Evaluation of Angiogenesis in the Ischemic Limb.

Development of collateral vessels in the ischemic limb was serially evaluated by calf blood pressure measurement and internal lilac arteriography immediately prior to transfection (day 0), and then in serial fashion at days 10 and 30 post-transfection. On each occasion, it was necessary to lightly anesthetize the animal with a mixture of Ketamine (10 mg/kg) and acepromazine (0.16 mg/kg) following premedication with xyazine (2.5 mg/kg). Following the final 30-day follow-up, the animal was sacrificed, and tissue sections were prepared from the hindlimb muscles in order to perform analysis of capillary density. These analyses are discussed in detail below.

Calf Blood Pressure Ratio.

Calf blood pressure was measured in both hindlimbs using a Doppler Flowmeter (Model 1050, Parks Medical Electronics, Aloha, Oreg.), immediately prior to transfection (day 0), as well as on days 10 and 30. On each occasion, the hindlimbs were shaved and cleaned; the pulse of the posterior tibial artery was identified using a Doppler probe; and the systolic pressure of both limbs was determined using standard techniques. Takeshita, et al., *J. Clin. Invest.*, 93:662–670 (1994). The calf blood pressure ratio was defined for each rabbit as the ratio of systolic pressure of the ischemic limb to systolic pressure of the normal limb.

Selective Internal Iliac Arteriography.

Collateral artery development in this ischemic hindlimb model originates from the internal lilac artery. Accordingly, selective internal lilac arteriography was performed on day 0 (immediately prior to transfection), and again on days 10 and 30 post-transfection as previously described. Takeshita, et al., *J. Clin. Invest.*, 93:662–670 (1994). A 3 Fr. end-hole infusion catheter (Tracker-18, Target Therapeutics, San Jose, Calif.) was introduced into the right common carotid artery through a small cutdown, and advanced to the internal lilac artery at the level of the interspace between the seventh lumbar and the first sacral vertebrae. Following intra-arterial injection of nitroglycerin (0.25 mg, SoloPak Laboratories, Franklin Park, Ill.), a total of 5 ml of contrast media (Isovue-370, Squibb Diagnostics, New Brunswick, N.J.) was then injected using an automated angiographic injector (Medrad, Pittsburgh, Pa.) programmed to reproducibly deliver a flow rate of 1 ml per sec. Serial images of the ischemic hindlimb were then recorded on 105-mm spot film at a rate of 1 film per sec for at least 10 sec. Following completion of arteriography, the catheter was removed and the wound was closed. All of the above-described procedures were completed without the use of heparin.

Morphometric angiographic analysis of collateral vessel development was performed as previously described. Takeshita, et al., *J. Clin. Invest.*, 93:662–670 (1994). A composite of 5-mm$^2$ grids was placed over the medical thigh area of the 4-sec angiogram. The total number of grid intersections in the medical thigh area, as well as the total number of intersections crossed by a contrast-opacified artery were counted individually by a single observer blinded to the treatment regimen. An angiographic score was calculated for each film as the ratio of grid intersections in the medial thigh.

Capillary Density and Capillary/Myocyte Ratio.

The effect of VEGF gene transfer upon anatomic evidence of collateral artery formation was further examined by measuring the number of capillaries in light microscopic sections taken from the ischemic hindlimbs. Takeshita, et al., *J. Clin. Invest.*, 93:662–670 (1994). Tissue specimens were obtained as transverse sections from the ischemic limb muscles at the time of sacrifice (day 30 post-transfection). Muscle samples were embedded in O.C.T. compound, (Miles, Elkhart, Ind.) and snap-frozen in liquid nitrogen. Multiple frozen sections (5 µm in thickness) were then cut from each specimen on a cryostat (Miles), so that the muscle fibers were oriented in a transverse fashion, and two sections then placed on glass slides. Tissue sections were stained for alkaline phosphate using an indoxyl-tetrazolium method to detect capillary endothelial cells (Ziada, et al., Cardiovasc. Res., 18:724–732 (1984)), and were then counterstained with eosin. Capillaries were counted under a 20x objective to determine the capillary density (mean number of capillaries per mm$^2$). A total of 20 different fields was randomly selected, and the number of capillaries counted. To ensure that analysis of capillary density was not overestimated due to muscle atrophy, or underestimated due to interstitial edema, capillaries identified at necropsy were also evaluated as a function of myocytes in the histologic section. The counting scheme used to compute the capillary/myocyte ratio was otherwise identical to that used to compute capillary density.

Reverse Transcription-Polymerase Chain Reaction (RT-PCR), Southern Blot Analysis, and Sequencing of RT-PCR Product.

The presence of human VEGF mRNA was detecting using RT-PCR. Arterial samples were obtained at 5 days post-transfection, and total cellular RNA was isolated using TRI REAGENT (Molecular Research Center, Cincinnati, Ohio) according to the manufacturer's instructions. Extracted RNA was treated with DNase I (0.5 µl, 10 U/µl, RNase-free, Message Clean kit, GenHunter, Boston, Mass.) at 37° C. for 30 min to eliminate DNA contamination. The yield of extracted RNA was determined spectrophotometrically by ultraviolet absorbance at 260 nm. To check that the RNA was not degraded and electrophoresed through a 1% non-denaturing miniagarose gel. 0.5 µg of each RNA sample was used to make cDNA in a reaction volume of 20 µl containing 0.5 mM of each deoxynucleotide triphosphate (Pharmacia, Piscataway, N.J.), 10 mM dithiothreitol, 10 units of RNasin (Promega, Madison, Wis.), 50 mM Tris-HCl (pH 8.3), 75 mM KCL, 3 mM MgCl$_2$, 1 µg random hexanucleotide primers (Promega), and 200 units of M-MLV reverse transcriptase (GIBCO BRL). For greater accuracy and reproducibility, master mixes for a number of reactions were made up and aliquoted to tubes containing RNA. Reactions were incubated at 42° C. for 1 hr, then at 95° C. for 5 min to terminate the reaction. Twenty µl of diethyl pyrocarbonate (DEPC) water was then added and 5 µl of the diluted reaction (⅛th) was used on the PCR analysis. The optimized reaction in a total volume of 20 µl contained 0.2 mM of each deoxynucleotide triphosphate, 3 mM MgCl$_2$, 2 µl PCR II buffer (Perkin-Elmer, Norwalk, Conn.; final concentrations, 50 mM KCL, 10 mM Tris-HCL), 5 ng/µl (13.77 pmoles) of each primer, and 0.5 units of AmpliTaq DNA polymerase (Perkin-Elmer). The PCR was performed on a 9600 PCR system (Perkin-Elmer) using microamp 0.2. ml thin-walled tubes. Amplification was for 40–45 cycles of 94° C. for 20 sec, 55° C. for 20 sec, and 72° C. for 20 sec, ending with 5 min at 72° C. To test for false positives, controls were included with no RNA and no reverse transcriptase. A pair of oligonucleotide primers (22 mers) was designed to amplify a 258 bp sequence from the mRNA of human VEGF. To ensure specificity and avoid amplification of endogenous rabbit VEGF, each primer was selected from a region which is not conserved among different species. Sequences of primers used were: 5'-GAGGGCAGAATCATCACGAAGT-3' (sense) SEQ. ID NO:1 ; 5'-TCCTATGTGCTGGCCTTGGTGA-3' (antisense) SEQ. ID NO:2. RT-PCR products were transferred from agarose gels to nylon membranes (Hybond, Amersham, Arlington Heights, Ill.). The probe was 5' end-labelled with T4 polynucleotide kinase and [β-$^{32}$P]ATP (Sambrook, et al., *Molecular Cloning: A Laboratory Manual*, Cold Spring Harbor Laboratory Press, (1989)) and hybridized to the nylon filters using Rapid Hybridization buffer (Amersham) according to manufacturer's instructions. To visualize hybridized bands, filters were exposed to X-ray film (Kodak Xar-5).

To confirm the identity of VEGF PCR products. DNA bands were excised from agarose gels, purified using Geneclean (BIO 101, La Jolla, Calif.), and sequenced directly (i.e. without subcloning) using dsDNA Cycle Sequencing System (GIBCO BRL) following the directions of manufacturer. The two VEGF primers used for PCR were 5' end-labeled with [β-$^{32}$P]ATP and T$_4$ polynucleotide kinase and used as sequencing primers to determine the sequence of both strands of the PCR product.

β-Galactosidase Staining of Transfected lilac Arteries.

To evaluate the efficiency of in vivo arterial gene transfer, β-galactosidase activity was determined by incubation of arterial segments with 5-bromo-4-chloro-3-indolyl β-D-galactosidase chromogen (X-Gall), Sigma) as previously described. Riessen, et al., *Hum. Gene Ther.*, 4:749–758 (1993). Following staining with X-Gal solution, tissues were paraffin-embedded, sectioned, and counterstained with nuclear fast red. Nuclear localized β-galactosidase expression of the plasmid pGSVLacZ cannot result from endogenous β-galactosidase activity; accordingly, histochemical identification of β-galactosidase within the cell nucleus was interpreted as evidence for successful gene transfer and gene expression. Cytoplasmic or other staining was considered non-specific for the purpose of the present study.

Statistics.

Results were expressed as means±standard deviation (SD). Statistical significance was evaluated using unpaired Student's t test for more than two means. A value of p<0.05 was interpreted to denote statistical significance.

Results

ELISA Assay for VEGF. To test the expression of the plasmid phVEGF$_{165}$ in vascular cells, culture supernatant of VEGF-transfected SMCs (1.48×10$^6$ cells/10 cm plate) was sampled at 3 days post-transfection, and analyzed by ELSA for VEGF protein. The media of VEGF-transfected SMCs contained an average of 1.5 µg of VEGF protein (n=3). In contrast, culture media of β-galactosidase-transfected SMCs (n=3) or non-transfected SMCs (n=3) did not contain detectable levels of VEGF protein.

RT-PCR, Southern Blot Analysis, and Sequencing of RT-PCR Product.

Figure 2A:
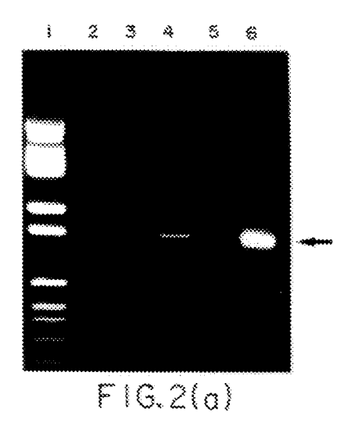
FIGS. 2(a), 2(b) and 2(c) illustrate (a) RT-PCR analysis of transfected arteries, (b) Southern blot analysis of RT-PCR products and (c) nucleotide sequence of the RT-PCR product from transfected rabbit lilac artery.
Figure 2B:
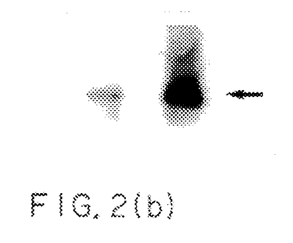
Figure 2C:
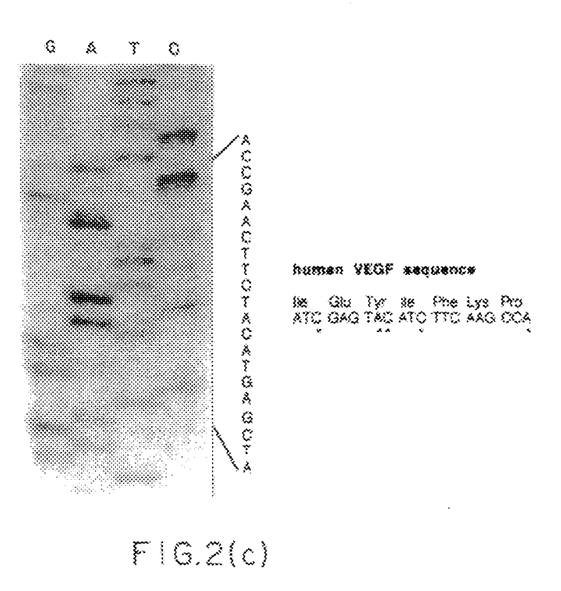
Figure 3A:
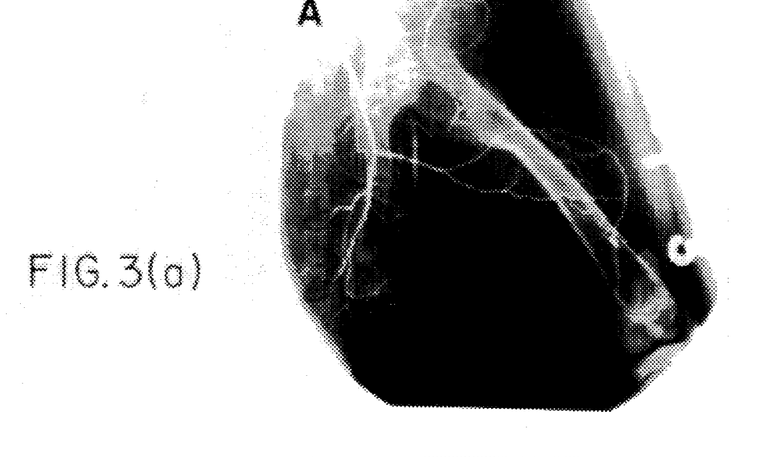
FIGS. 3A, 3B, 3C, 3D, 3E and 3F comprise internal lilac angiography of a control rabbit at (A) day 0 (pre-transfection), (B) day 10, and (C) day 30 post-transfection, and of a VEGF-transfected rabbit at (D) day 0, (E) day 10, and (F) day 30 post-transfection. In contrast to the control, angiographic examination of the VEGF-transfected animal discloses extensive collateral artery formation.
Figure 3B:
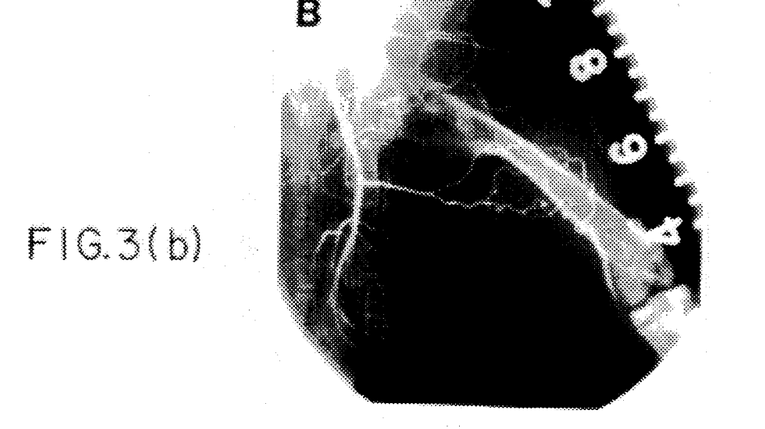
Figure 3C:
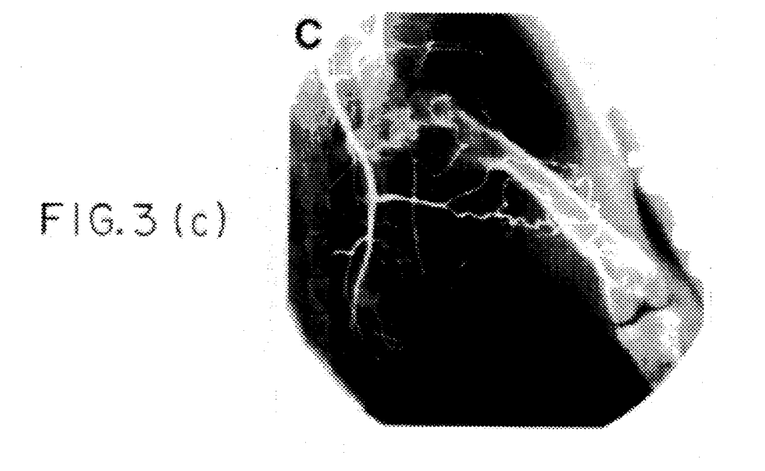
Figure 3D:
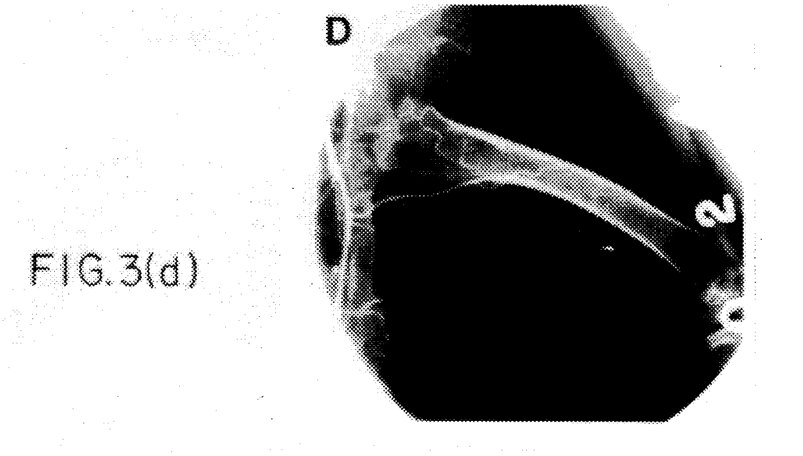
Figure 3E:
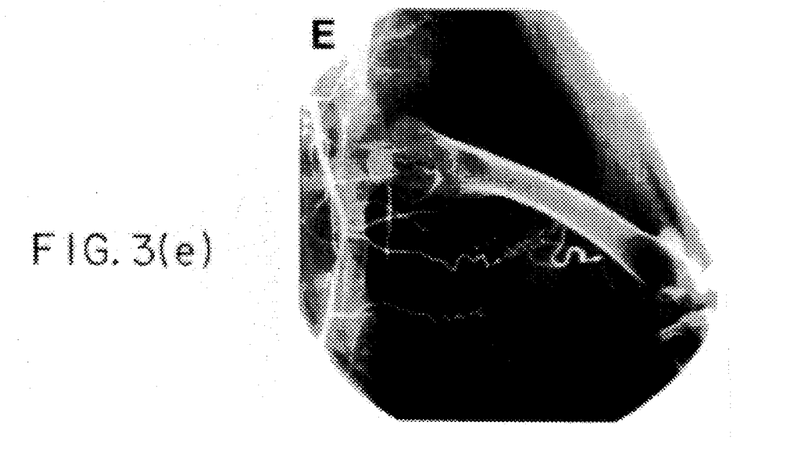
Figure 3F:
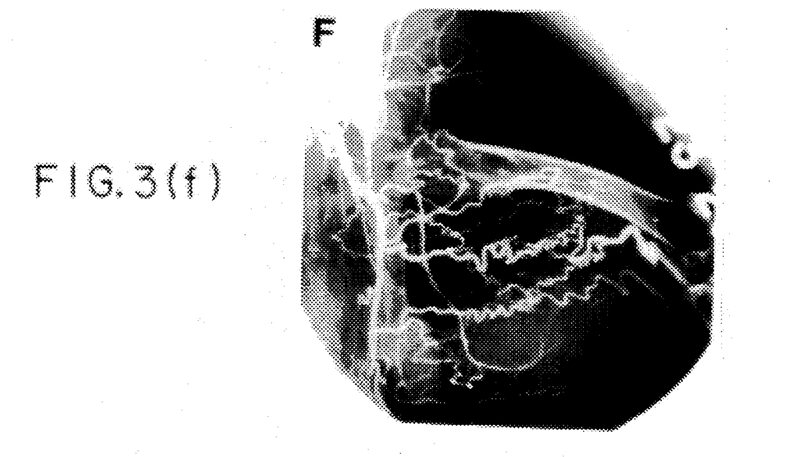

To confirm expression of human VEGF gene in transfected rabbit lilac arteries in vivo, we analyzed transfected arteries for the presence of human VEGF mRNA by RT-PCR. As indicated above, to ensure the specificity of RT-PCR for human VEGF mRNA resulting from successful transfection (versus endogenous rabbit VEGF mRNA), primers employed were selected from a region which is not conserved among different species. Arteries were harvested at 5 days post-transfection. The presence of human VEGF mRNA was readily detected in rabbit SMC culture (n=3) and rabbit lilac arteries (n=3) transfected with phVEGF$_{165}$. Rabbit lilac arteries transfected with pGSVLacZ (n=3) were negative for human VEGF mRNA (FIG. 2(a)). Southern blot analysis was used to further confirm that the 158 bp bands obtained by RT-PCR did in fact correspond to the region between the two primers (FIG. 2(b)). Direct sequencing of the RT-PCR product document that this band represented the human VEGF sequence (FIG. 2(c)).

Angiographic Assessment.

Figure 4A:
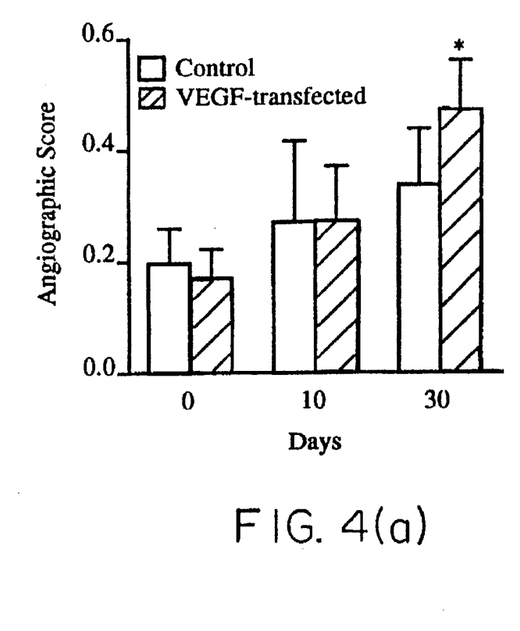
FIGS. 4(a), 4(b) and 4(c) are graphs illustrating the effect of VEGF-transfection on revascularization in an ischemic limb model.

The development of collateral vessels in the 5 rabbits transfected with phVEGF$_{165}$ and 6 rabbits transfected with pGSVLacZ was evaluated by selective internal lilac angiography. FIG. 3 illustrates representative internal lilac angiogram recorded from both control and VEGF-transfected animals. In control animals, collateral artery development in the medial thigh typically appeared unchanged or progressed only slightly in serial angiogram recorded at days 0, 10, and 30 (FIGS. 3(a–c)). In contrast, in the VEGF-transfected group, marked progression of collateral artery was observed between days 10 and 30 (FIGS. 3, (d–f)). Morphometric analysis of collateral vessel development in the media thigh was performed by calculating the angiographic score as described above. At baseline (day 0), there was no significant difference in angiographic score between the VEGF-transfected and control groups (day 0:0.17±0.02 vs 0.20±0.06, p=ns). By day 30, however, the angiographic score in VEGF-transfected group was significantly higher that in control group (0.47±0.09 vs 0.34±0.10, p<0.05) (FIG. 4(a)).

Figure 4B:
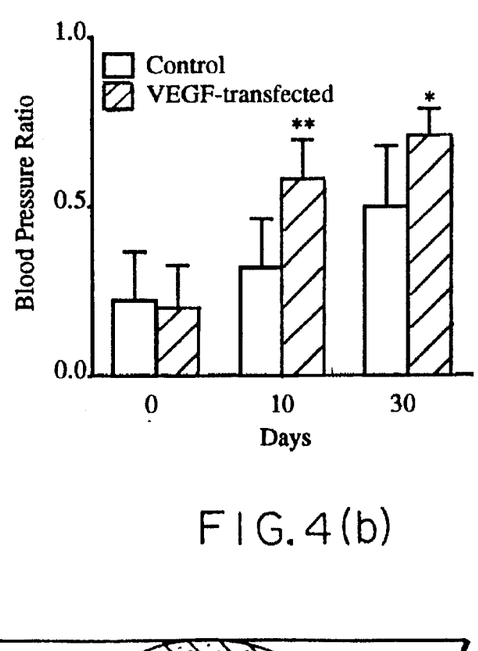

Calf Blood Pressure Ratio (FIG. 4(b)).

Reduction of the hemodynamic deficit in the ischemic limb following VEGF-transfection was confirmed by measurement of calf blood pressure ratio (ischemic/normal limb). The calf blood pressure ratio was virtually identical in both groups prior to transfection (0.23±0.12 in VEGF-transfected animals, p=ns). By day 10 post-transfection, the blood pressure ration for VEGF-transfected rabbits was significantly higher than for the control rabbits (0.60±0.12 vs 0.32±0.14, p<0.01). At day 30, the blood pressure ratio for the VEGF-transfected group continued to exceed that of controls (0.70±0.08 vs 0.50±0.18, p<0.05).

Figure 4C:
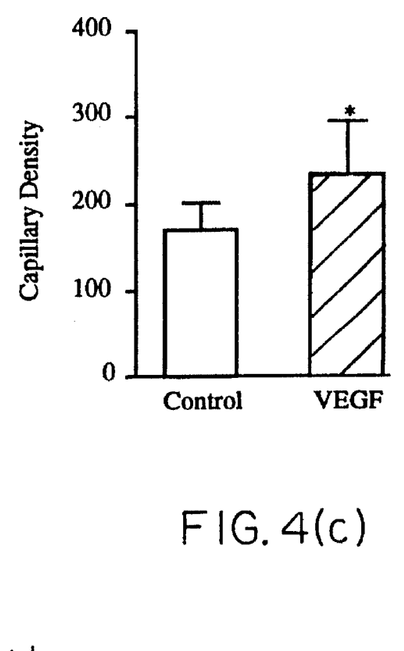
Figure 5A:
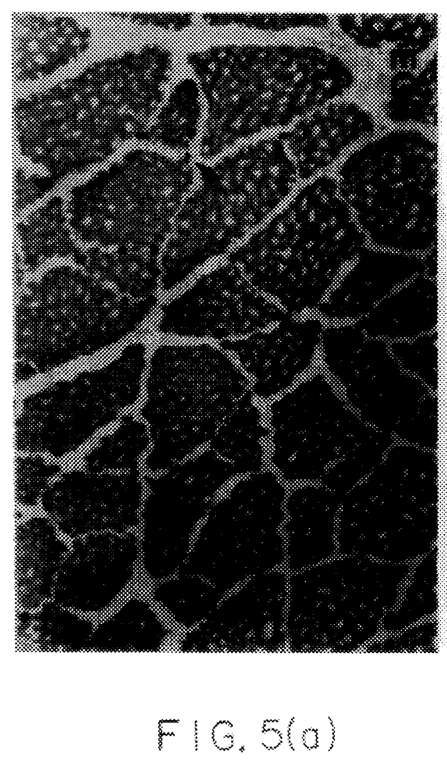
FIGS. 5(a) and 5(b) illustrate alkaline phosphatase staining of ischemic hindlimb muscle, counterstained with eosin.
Figure 5B:
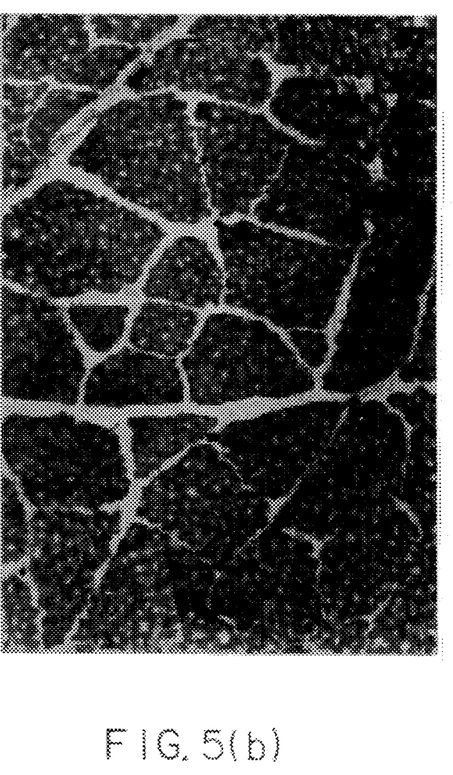

Capillary Density and Capillary/Myocyte Ratio (FIGS. 4(c), 5).

A favorable effect of VEGF-transfection upon revascularization was also apparent at the capillary level. The medial thigh muscles of the ischemic limbs were histologically examined at day 30 post-transfection. Analysis of capillary density disclosed a value of $233.0±60.9/mm^2$ in VEGF-transfected group versus $168.7±31.5/mm^2$ in the control group (p<0.05). Analysis of capillary/myocyte ratio disclosed a value of 0.67±0.15 in the VEGF-transfected group versus 0.48±0.10 in the control group (p<0.05).

β-Galactosidase Staining of Transfected Iliac Arteries.

To evaluate the efficiency of in vivo arterial gene transfer, transfected lilac arteries were harvested at 5 days post-transfection, and were used for β-galactosidase histochemical analysis. In arteries transfected with nuclear targeted β-galactosidase, evidence of successful transfection, indicated by dark blue nuclear staining, was observed in only<0.5% of total arterial cells. Arteries transfected with phVEGF$_{165}$ were negative for nuclear staining.

EXAMPLE 3

Comparison of Double-Balloon Catheter Technique and Hydrogel-Coated Balloon Catheter Technique Methods Recombinant Adenoviral Vectors Replication-defective recombinant adenoviral vectors, based on human adenovirus 5 serotype, were produced as previously described. Quantin, et al., *Proc. Nat. Acad. Sci. USA*, 89:2581–2584 (1992); Stratford-Perricaudet, et al., *J. Clin. Invest.*, 90:626–630 (1992); and Rosenfeld, et al., *Cell*, 68:143–155 (1992). Ad-RSVβgal contains the *Escherichia coil* lac Z gene and the SV40 early region nuclear localization sequence (nls). The nlslacZ gene encodes a nuclear-targeted β-galactosidase under the control of the Rous sarcoma virus promoter. Ad-RSVmDys, used as a negative control, contains a human "minidystrophin" cDNA under the control of the same promoter. Ragot, et al., *Nature*, 361:647–650 (1993).

In Vivo Percutaneous Gene Transfer Procedures

All animal procedures were approved by the Institutional Animal Care and Use Committees of Faculte Bichat and St. Elizabeth's Hospital. Gene transfer was performed in the external lilac artery of 29 New Zealand white rabbits under general anesthesia and sterile conditions. Anesthesia was induced with intramuscular acepromazine and maintained with intravenous pentobarbital. Adenoviral stocks were used within 30 minutes of thawing.

1. Double-balloon catheter technique.

In 15 animals, Ad-RSVβgal ($2.10^9$ to $2.10^{10}$ plaque forming unites {pfu} in 2 ml PBS) was transferred to the right lilac artery, either normal (n=9) or previously denuded (n=6), using a 4 French double-balloon catheter (Mansfield Medical, Boston Scientific Corp., Watertown, Mass.) as previously described. Nabel, et al., *Science*, 244:1342–1344 (1989). The catheter was positioned in a segment of the artery which lacked angiographically visible side branches. The viral solution was maintained in contact with the arterial wall for 30 min. The left lilac artery of the same 15 animals was used as a control: in 7 animals no catheter was inserted, in 6 animals the endothelium was removed using balloon abrasion, and, in the 2 other animals, a double-balloon catheter was used in infuse Ad-RSVmDys ($2.10^9$ pfu in 2 ml PBS).

2. Hydrogel-Coated Balloon Catheter Technique.

In 14 animals, a hydrogel-coated balloon catheter was used (Slider™ with Hydroplus®, Mansfield Medical, Boston Scientific Corp., Watertown, Mass.). The balloon diameter (either 2.5 or 3.0 mm), was chosen to approximate a 1.0 balloon/artery ratio based on caliper measurement of magnified angiographic frames. Ad-RSVβgal ($1–2.10^{10}$ pfu in 100 µl PBS) was applied to the polymer-coated balloon using a pipette as described above. The catheter was introduced into the right femoral artery through a protective sheath, the balloon was inflated at 1 atm, and the assembly was then advanced over a 0.014" guide wire to the external lilac artery where, after balloon deflation, the catheter alone was advanced 2 cm further and the balloon inflated for 30 minutes at 6 atm (ensuring nominal size of the inflated balloon). The contralateral lilac artery was in each case used as a control: in 9 animals no catheter or virus was introduced, in 2 the endothelium was removed, while in 3 a hydrogel-coated balloon catheter was used to transfer Ad-RSVmDys.

Detection of lacZ Expression in the Arterial Wall.

Three to seven days after transfection, the animals were sacrificed by pentobarbital overdose. To assess nlslacZ gene expression, the arteries were harvested and stained with X-Gal reagent (Sigma) for 6 hours, at 32° C., as previously described. Sanes, et al., *EMBO J.*, 5:3133–3142 (1986). Samples were then either mounted in OCT compound (Miles Laboratories Inc., Ill.) for cryosectioning or embedded in paraffin, cut into 6-µm sections, and counterstained with hematoxylin and eosin or elastic trichrome. Expression of nlslacZ gene was considered positive only when dark blue staining of the nucleus was observed. To determine which cell types within the arterial wall expressed the transgene, immunohistochemical staining of X-Gal-stained arterial sections was performed, using a mouse monoclonal anti-α-actin primary antibody specific for vascular smooth muscle (HHF-35, Enzo Diagnostics, Farmingdale, N.Y.), and then a polyclonal peroxidase-labeled anti-mouse immunoglobulin G secondary antibody (Signet Laboratories, Dedham, Mass.).

Morphometric Analysis of nlslacZ Gene Expression in the Media.

For each transfected iliac artery, at least 2 samples were taken from the target-zone, and from each sample, at least 3 sections were examined by light microscopy after X-gal staining. Due to the heterogeneity of β-galactosidase activity on gross examination, the percentage of transfected medial cells per artery section was determined in regions showing high β-galactosidase activity by counting stained versus total nuclei. The total numbers of studied medial cells were $14.10^3$ (n=50 sections) in the double-balloon catheter and the hydrogel-coated balloon catheter groups respectively.

Detection of Remote$^{nlslacZ}$ Gene Transfer and Expression.

Tissue samples from liver, brain, testes, heart, lungs, kidneys, contralateral limb skeletal muscle, and arterial segments adjacent to the treated arterial site were harvested immediately after sacrifice. For each specimen, nlslacZ gene presence and expression were assessed by polymerase chain reaction (PCR) and histochemistry (X-gal staining) respectively.

For PCR, genomic DNA was extracted from tissues by standard techniques. DNA amplification was carried out using oligodeoxynucleotide primers designed to selectively amplify Ad-RSVβgal DNA over endogenous β-galactosidase gene by placing one primer in the adenovirus sequence coding for protein 9 and the other primer in the lacZ sequence (5'-AGCCCGTCAGTATCGGCGGAATTC-3' (SEQ ID NO:3) and 5'-CAGCTCCTCGGTCACATCCAG-3' (SEQ ID NO:4) respectively, Genset, Paris, France). The reactions were performed in a DNA thermocycler (GeneAmp PCR System 9600, Perkin Elmer Cetus, Norwalk, Conn.) following 2 different protocols: a hold at 95° C. for 3 min, 35 or 45 cycles of 95° C. for 30 s, 65° C. for 40 s, and 72° C. for 1 min, then a final extension at 72° C. for 5 min. When PCR was performed on plasmid DNA containing the nlslacZ gene used for the preparation of the adenoviral vector, or on positive liver samples obtained by deliberate systemic injection of Ad-RSVβgal, the amplification reaction produced a 700 bp DNA fragment. To determine sensitivity of these procedures, DNA was extracted from liver of uninfected rabbits, aliquoted into several tubes, and spiked with dilutions of the plasmid containing the nlslacZ gene and used as a positive control. Following the amplification protocols described above, it was determined that the 35- or 45-cycle PCR could detect one copy of the nlslacZ gene in $3.10^2$ and $3.10^4$ cells respectively. DNA extractions and amplifications were performed simultaneously and in duplicate for studied tissues and positive controls.

Each tissue sample was also processed for histochemical analysis following the same protocol described for the arteries. For each specimen, at least 3 different segments were obtained, embedded in paraffin, and cut into at least 5 sections. Sections were counterstained with hematoxylin and eosin, and examined by light microscopy for the presence of deep blue nuclei indicative of β-galactosidase expression. The number of positive cells as well as the total number of cells were counted. The total number of cells examined per sample ranged from $25.10^3$ to $115.10^3$.

Statistics

Results are expressed as mean±standard deviation (SD). Comparisons between groups were performed using Student's t test for unpaired observations. A value of p<0.05 was accepted to denote statistical significance.

Results

Histological and Histochemical Analyses of Transfected Arteries Following Double-Balloon Catheter Delivery Gross examination of all the arteries (n=15) following X-gal staining showed punctiform, heterogeneous, blue staining on the luminal aspect of the arteries, always limited to the area between the two balloons. For the 9 normal arteries, microscopic examination disclosed dark blue nuclear staining, confined entirely to the endothelium. In contrast, when endothelial abrasion preceded transfection (n=6), X-gal staining imparted a mottled appearance to the luminal aspect of the artery. In these cases, microscopic examination showed that the endothelium had been removed and that the site of X-gal staining was subjacent to the intact internal elastic lamina, involving sparse medial cells. The identity of the transfected medial cells as smooth muscle cells was confirmed by immunohistochemical staining with monoclonal anti-α-actin antibody. Control arteries showed no nuclear blue staining.

Histological and Histochemical Analysis of Transfected Arteries Following Hydrogel-Coated Balloon Catheter Delivery Gross examination of all the arteries after X-gal staining (n=14) showed dark blue, heterogeneous staining of the transfected site with a sharp boundary between the transfected segment and the bordering proximal and distal segments. Microscopic examination showed no residual intact endothelium; the continuity of the internal elastic lamina, in contrast, appeared preserved without apparent disruption. In the areas showing evidence of β-galactosidase activity on gross examination, light microscopic examination revealed nearly continuous layers of cells with dark blue nuclear staining, generally limited to the superficial layers of the media; occasionally, sparsely distributed cells from deeper layers of the media expressed the transgene as well. Staining with monoclonal anti-α-actin antibody confirmed that transfected cells were vascular smooth muscle cells. No evidence of nuclear β-galactosidase activity was seen in control arteries.

Morphometric Analysis of nlslacZ Gene Expression in the Media.

The percentage of transduced cells per artery section in regions showing high β-galactosidase activity was significantly higher in the hydrogel-coated balloon catheter group than in the double-balloon catheter group (6.1±2.3% vs. 0.4±0.6%, p<0.0001).

Detection of Remote lacZ Gene Transfer and Expression in Other Organs

In all animals of both groups, gross and microscopic examination of X-gal stained tissue samples from liver, brain, testes, heart, lungs, kidneys, contralateral limb skeletal muscle, and arterial segments adjacent to the treated arterial site failed to show expression of nuclear-targeted β-galactosidase, except in the liver of one rabbit in the double-balloon catheter group which disclosed a limited area of nuclear and peri-nuclear blue staining. In this area, less than $1/2.10^3$ cells expressed β-galactosidase. In a few macrophages limited to samples removed from the lungs and testes of one hydrogel-coated balloon catheter treated rabbit, blue staining of the cytoplasm without nuclear staining was observed; the exclusively cytoplasmic location of β-galactosidase activity in these cases, however, suggested that staining resulted from endogenous β-galactosidase.

All of the above tissue samples were then screened by PCR. When the PCR was run for 35 cycles, the presence of DNA sequence specific for Ad-RSVβgal was non-detectable, including in tissue samples from those animals with the highest percentage of transfected lilac arterial cells. Using an optimized protocol of 45 cycles, however, PCR was positive in the single liver that was observed to express β-galactosidase, but in none of the other tissues.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

growth factor, tumor necrosis factor α, hepatocyte growth factor and insulin like growth factor and having an operably linked secretory signal sequence or a first DNA encoding a modified angiogenic protein selected from the group consisting of acidic and basic fibroblast growth factors, vascular endothelial growth factor, epidermal growth factor, trans-

What is claimed is:

1. A method for inducing the formation of new blood vessels in a desired target tissue in a human host, comprising contacting an arterial cell in an artery or blood vessel via a balloon catheter coated with a hydrogel polymer admixed with a first DNA encoding an angiogenic protein selected from the group consisting of acidic and basic fibroblast growth factors, vascular endothelial growth factor, epidermal growth factor, transforming growth factor α and β, platelet-derived endothelial growth factor, platelet-derived forming growth factor α and β, platelet-derived endothelial growth factor, platelet-derived growth factor, tumor necrosis factor α, hepatocyte growth factor and insulin like growth factor having an operably linked secretory signal sequence, wherein said angiogenic protein induces new blood vessel formation when expressed in said target tissue in an amount effective to induce new blood vessel formation.

2. The method of claim 1, wherein the angiogenic protein is vascular endothelial growth factor.

3. The method of claim 1, wherein the hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides.

4. The method of claim 1, wherein the hydrogel polymer is a polyacrylic acid polymer.

5. The method of claim 1, wherein the hydrogel polymer is admixed with a second DNA encoding an angiogenic protein selected from the group consisting of acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor and having an operably linked secretory signal sequence or a second DNA encoding a modified angiogenic protein selected from the group consisting of acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor having an operably linked secretory signal sequence, wherein said angiogenic protein induces new blood vessel formation when expressed in said target tissue in an amount effective to induce new blood vessel formation, and wherein said second DNA is not the same as said first DNA.

6. A method for inducing the formation of new blood vessels in a desired target tissue in a human host, comprising contacting an arterial cell in an artery or blood vessel via a balloon catheter coated with a hydrogel polymer admixed with DNA encoding vascular endothelial growth factor and which is expressed in an amount effective to induce new blood vessel formation.

* * * * *